United States Patent [19]
Richards et al.

[11] Patent Number: 5,882,520
[45] Date of Patent: *Mar. 16, 1999

[54] USE OF ARABINOGALACTAN IN AQUEOUS TWO PHASE EXTRACTIONS

[75] Inventors: Geoffrey N. Richards; Merilyn Manley-Harris, both of Missoula, Mont.

[73] Assignee: The University of Montana, Missoula, Mont.

[*] Notice: This patent issued on a continued prosecution application filed under 37 CFR 1.53(d), and is subject to the twenty year patent term provisions of 35 U.S.C. 154(a)(2).

[21] Appl. No.: 548,849

[22] Filed: Oct. 26, 1995

[51] Int. Cl.$^6$ .............................. C12N 9/00; B01D 11/00
[52] U.S. Cl. .................... 210/632; 210/634; 210/639; 252/364; 435/183; 435/267; 435/816
[58] Field of Search ..................................... 210/634, 638, 210/639, 511, 602, 635, 631, 632; 536/1.1; 252/364; 436/178; 435/183, 201, 816, 262, 267, 272

[56] References Cited

U.S. PATENT DOCUMENTS

| | | | |
|---|---|---|---|
| 4,094,971 | 6/1978 | Chedid et al. | 424/92 |
| 4,390,450 | 6/1983 | Gibson et al. | 426/568 X |
| 4,579,661 | 4/1986 | Gustafsson et al. | 210/635 |
| 4,743,550 | 5/1988 | Ananthapadmanabhan et al. | 435/183 |
| 4,921,796 | 5/1990 | Rozzell | 435/97 |
| 4,980,065 | 12/1990 | Hsu | 210/634 |
| 5,041,226 | 8/1991 | Shibata et al. | 210/635 |
| 5,078,886 | 1/1992 | Hsu | 210/635 |
| 5,093,254 | 3/1992 | Giuliano et al. | 435/183 |
| 5,116,969 | 5/1992 | Adams et al. | |
| 5,478,576 | 12/1995 | Jung et al. | 536/1.11 |

FOREIGN PATENT DOCUMENTS

| | | |
|---|---|---|
| 60-219201 | 4/1984 | Japan . |
| 85-314077150 | 6/1994 | Japan . |

OTHER PUBLICATIONS

Albertsson, P., *Partition of Cell Particles and Macromolecules,* Third edition, John Wiley & Sons, Title Page and Table of Contents, 7 pgs. (1986).

Albertsson, P., et al., "Phase Diagrams," *Methods In Enzymology,* 228, 3–13 (1994).

(List continued on next page.)

*Primary Examiner*—Joseph W. Drodge
*Attorney, Agent, or Firm*—Mueting, Raasch, & Gebhardt, P.A.

[57] ABSTRACT

Aqueous two phase systems are provided which permit the extractive separation of biological materials. In a preferred embodiment, an aqueous solution of arabinogalactan defines at least one phase, and an aqueous solution of a second solute, such as a polyether, defines at least one other phase. In one embodiment, an aqueous two phase system is provided in which one phase is defined by an aqueous solution containing predominantly ultrarefined arabinogalactan, and the other phase is defined by an aqueous solution containing predominantly a polymer such as a poly(ethylene glycol). Biological materials which can be extracted and separated from mixtures using the aqueous two phase systems include cells, organelles, macromolecules and organic molecules. The aqueous two phase systems can be used in wide range of different applications including in bioconversions for the production and separation of enzyme reaction products. The aqueous two phase systems can be used to extract a wide range of biological materials from aqueous mixtures inexpensively on a large scale, while maintaining the biological activity of the materials.

28 Claims, 2 Drawing Sheets

OTHER PUBLICATIONS

Armbruster, F., "Use of Cyclohexane in the Production of Pure alpha– and beta–Cyclodextrins," *Proceedings of the Fourth International Symposium on Cyclodextrins,* Munich, West Germany, Apr. 20–22, 33–39 (1988).

Bamberger, S., et al., "Preparation of Phase Systems and Measurement of Their Physicochemical Properties," *Partitioning in Aqueous Two–Phase Systems,* Academic Press, Inc., Chapter 3, 85–130 (1985).

Bogračeva, T., et al., "Über die thermodynamische Verträglichkeit von Gummiarabicum und makromolekularen Komponenten der Globulinfraktion der Bäckerhefe," *Die Nahrung,* 27, 735–740 (1983).

Bogracheva, T., et al., "Use of Polysaccharides to Remove Lipids from the Protein Globulin Fraction of Baker's Yeast," *Carbohydrate Polymers,* 2, 163–170 (1982).

Brooks, D., et al., "Preparation and Analysis of Two–Phase Systems," *Methods In Enzymology,* 228, 14–27 (1994).

Clark, A., et al., "Pollen–stigma interactions: Identification and characterization of surface components with recognition potential," *Proc. Natl. Acad. Sci.,* 76, 3358–3362 (1979).

Delbourg, M., et al., "Effect of PEG and other Additives on Cyclodextrin Production by *Bacillus macerans* Cyclomaltodextrin–Glycosly–Transferase," *Biotechnology Letters,* 15, 157–162 (1993).

Ekman, K., et al., "Some Physicochemical Properties of Arabinogalactan from Western Larch (*Larix occidentalis* Nutt.)," *Tappi,* 45, 477–481 (1962).

Groman, E., et al., "Arabinogalactan for Hepatic Drug Delivery," *Bioconjugate Chem.,* 5, 547–556 (1994).

Hagmar, B., "Liver Lectins, Adhesion Molecules in Experimental Metastasis," *Bakteriol. Suppl.,* 25, 138–145 (1994).

Hammar, L., "Concentration of Biomaterials: Virus Concentration and Viral Protein Isolation," *Methods In Enzymology,* 228, 640–658 (1994).

Han, I., et al., "Production of Cyclodextrin from Raw Starch in the Agitated Bead Reaction System and its Reaction Mechanism," *Kor. J. Appl. Microbiol. Biotechnol.,* 19, 163–170 (1991).

Hashimoto, H., et al., "Concentration of the Conversion Mixture Solution by Using Reverse Osmosis Membrane," *J. Jpn. Soc. Starch Sci.,* 32, 307–311 (1985).

Hayashida, K., et al., "Enhancement of Enzymatic Production of Cyclodextrins by Adding Polyethylene Glycol or Polypropylene Glycol," *Journal of Fermentation and Bioengineering,* 73, 239–240 (1992).

Hayashida, K., et al., "Enzymatic Hydrolysis of Soluble Starch in a Polyethylene Glycol–Dextran Aqueous Two–Phase System," *Journal of Fermentation and Bioengineering,* 69, 240–243 (1990).

Hosono, K., et al, "Separation of yeast protoplasts from membrane ghosts using an aqueous two–phase system," *Biochimica et Biophysica Acta,* 855, 189–192 (1986).

Hosseini, J., et al., "Comparison of Two Separation Techniques for the Determination of Blood Mononuclear Cell Magnesium Content," *Journal of the American College of Nutrition,* 4, 361–368 (1983).

Johansson, G., "Affinity Partitioning in PEG–containing Two phase Systems, Section 5.2:System Parameters," *Poly(Ethylen Glycol) Chemistry: Biotechnical and Biomedical Applications,* J. Milton Harris, ed., Plenum Press, NY, pp. 75–84 (1992).

Johansson, G., "Uses of Poly(ethylene Glycol) with Charged or Hydrophobic Groups," *Methods In Enzymology,* 228, 64–75 (1994).

Kim, T., et al., "Enzymatic Production of Cyclodextrins from Milled Corn Starch in an Ultrafiltration Membrane Bioreactor," *Biotechnol. and Bioeng.,* 41, 88–94 (1993).

Kobata, A., "Glycobiology: An Expanding Research Area in Carbohydrate Chemistry," *Acc. Chem. Res.,* 26, 319–324 (1993).

Köhler, K., et al., "Uses of Fusions of β–Galactosidase and Peptides to Proteins," *Methods In Enzymology,* 228, 627–640 (1994).

Kroner, K., et al., "Extractive Enzyme Recovery: Economic Considerations," *Process Biochem.,* 19, 170–179 (1984).

Kroner, K., et al., "Evaluation of Crude Dextran as Phase––Forming Polymer for the Extraction of Enzymes in Aqueous Two–Phase Systems in Large Scale," *Biotechnol. and Bioeng.,* 24, 1015–1045 (1982).

Larsson, M., et al., "Characterization of Aqueous Two–Phase Systems Based on Polydisperse Phase Forming Polymers: Enzymatic Hydrolysis of Starch in a PEG–Starch Aqueous Two–Phase System," *Biotechnol. and Bioeng.,* 31, 979–983 (1988).

Larsson, M., et al., "Integration of Bioconversion and Downstream Processing: Starch Hydrolysis in an Aqueous Two–Phase System," *Biotechnol. and Bioeng.,* 33, 758–766 (1989).

Lawrence, A., "Arabinogalactan," *Natural Gums for Edible Purposes,* Noyes Data Corporation, NJ, Title Page, Table of Contents, and pp. 1–16 (1976).

Layne, E., "Spectrophotometric and Turbidimetric Methods for Measuring Proteins," *Methods in Enzymology,* 3, 447–455 (1957).

Lee, Y., et al., "Enhancement of enzymatic production of cyclodextrins by organic solvents," *Enzym. Microb. Technol.,* 13, 499–503 (1991).

Lee, R., et al., "New Synthetic Cluster Ligands for Galactose/N–Acetylgalactosamine–Specific Lectin of Mammalian Liver," *Biochem.,* 23, 4255–4261 (1984).

Ling, T., et al., "Reppal PES—a Starch Derivative for Aqueous Two–Phase Systems," *Carbohydr. Polymers,* 11, 43–54 (1989).

Lowry, O., et al., "Protein Measurement with the Folin Phenol Reagent," *J. Biol. Chem.,* 193, 265–275 (1951).

Majumdar, T., et al., "Cross–linked arabinogalactan: A new affinity matrix for the purification of *Ricinus communis* lectins," *Experientia,* 34, 979–980 (1978).

Mattiasson, B., "Bioconversions in Aqueous Two–Phase Systems: An Alternative to Conventional Immobilization," *Methods in Enzymology,* 137, 657–667 (1988).

Muchmore, A., et al., "Spontaneous Cytotoxicity by Human Peripheral Blood Monocytes: Inhibition by Monosaccharides and Oligosoaccharides," *Immunobiol.,* 158, 191–206 (1981).

Nazareth, M., et al., "Studies on Larch Arabogalactan I," *J. Pharm. Sci.,* 50, 560–563 (1961).

Nazareth, M., et al., "Studies on Larch Arabogalactan II," *J. Pharm. Sci.,* 50, 564–567 (1961).

Nguyen, A., et al., "Applications of pullulan in aqueous two–phase systems for enzyme production, purification and utilization," *Appl. Microbiol. Biotechnol.,* 27, 341–346 (1988).

Owens, H., "The Viscosities of Arabogalactan Solutions," *J. Am. Chem. Soc.,* 62, 930–932 (1940).

*Poly(Ethylene Glycol) Chemistry,* J. Milton Harris, ed., Plenum Press, NY, Title Page, Table of Contents, Chapters 4–6, 57–102 (1992).

Rendleman, J., "Enhanced production of cyclomaltooctaose (γ–cyclodextrin) through selective complexation with $C_{12}$ cyclic compounds," *Carbohydr. Res.,* 230, 343–359 (1992).

Starnes, R., "Industrial Potential of Cyclodextrin Glycosyl Transferases," *Cereal Foods World,* 35, 1094–1099 (1990).

Stoscheck, C., "Quantitation of Protein," *Methods in Enzymology,* 182, 50–68 (1990).

Stout, A., "Larch Arabogalactan," *Industrial Gums,* R.L. Whistle, ed., Academic Press, NY, Chapter 12, 307–310 (1959).

Sturesson, S., et al., "Partition of Macromolecules and Cell Particles in Aqueous Two–Phase Systems Based on Hydroxypropyl Starch and Poly(ethylene Glycol)," *Appl. Biochem. Biotechnol.,* 26, 281–295 (1990).

Szlag, D., et al., "A Low–Cost Aqueous Two Phase System for Enzyme Extraction," *Biotechnol. Techniques,* 2, 277–282 (1988).

Szlag, D., et al., "A Low–Cost Aqueous Two–Phase System for Affinity Extraction," *ACS Symposium Series,* 419, Chapter 4, 71–86 (1990).

Timell, T., "Wood Hemicelluloses: Part II," *Adv. Carbohydr. Chem.,* 20, 409–483 (1965).

Tjerneld, F., et al., "Aqueous two–phase systems for biotechnical use," *Bioseperation,* 1, 255–263 (1990).

Tjerneld, F., et al., "Enzymatic Hydrolysis of Cellulose in Aqueous Two–Phase Systems. I. Partition of Cellulases from *Trichoderma reesei,*" *Biotechnol. and Bioengineering,* 27, 1036–1043 (1985).

Tjerneld, F., et al., "Enzymatic Hydrolysis of Cellulose in Aqueous Two–Phase Systems. II. Semicontinuous Conversion of a Model Substrate, Solka Floc BW 200," *Biotechnol. and Bioengineering,* 27, 1044–1050 (1985).

Tolstoguzov, V., "Concentration and purification of proteins by means of two–phase systems: membraneless osmosis process," *Food Hydrocolloids,* 2, 195–207 (1988).

Walter, H., et al., "Partitioning Procedures and Techniques: Cells, Organelles, and Membranes," *Methods in Enzymology,* 228, 42–63 (1994).

Yates, E., et al., "Investigations into the occurrence of plant cell surface epitopes in exudate gums," *Carbohydrate Polymers,* 24, 281–286 (1994).

Zhuravskaya, N., et al., "Concentration of proteins as a result of the phase separation of water–protein–polysaccharide systems; Part 1. Phase equilibria in water–milk proteins–polysaccharide systems," *Die Nahrung,* 30, 591–599 (1986).

Zhuravskaya, N., et al., "Concentration of proteins as a result of the phase separation of water–protein–polysaccharide systems; Part 2. Concentration of milk proteins," *Die Nahrung,* 30, 601–613 (1986).

USE OF ARABINOGALACTAN IN AQUEOUS TWO PHASE EXTRACTIONS

BACKGROUND OF THE INVENTION

The present invention is generally in the area of aqueous two phase systems for use in partitioning components in an aqueous solution.

The study of biological systems requires efficient means of separation which are mild enough such that biological activity is retained throughout the process. Aqueous two-phase systems, which are both mild and efficient, have been in use in laboratories for about thirty years. Per-Ake-Albertsson, *Partition of Cell Particles and Macromolecules*, 3rd Edn., John Wiley & Sons, New York, 1986. Aqueous two phase systems form when two water soluble polymers are dissolved in water. The aqueous two phase systems contain mainly water, with the first polymer predominating in one phase and the second polymer predominating in the other phase. Due to their high water content, both equilibrium phases provide a suitable environment for biological macromolecules. When a mixture of proteins is added to an aqueous two phase polymer system, each type of protein partitions uniquely between the two phases.

There has been an increase in interest in this type of system, both industrially and in research applications, during the past few years. Walter, H. and Johansson, G., Eds., *Methods in Enzymology*, Vol. 228 (1994). The system can be used to separate a desired product from a cell culture. For example, an enzyme can be partitioned into one easily-removable phase while cell debris and unwanted molecules remain in the other phase. Alternatively, an enzyme can be confined to one phase and supplied with a substrate, the products of the fermentation of that substrate being extracted into the other phase. This process is a form of extractive bioconversion.

Applications of this methodology in the biotechnology industry are described in a review by Hustedt et al., and economic considerations have been discussed by Kroner et al. Hustedt et al., "Applications of Phase Partitioning in Biotechnology", in *"Partitioning in Aqueous Two-Phase Systems: Theory, Methods, Uses and Applications to Biotechnology"*, Academic Press, New York, 1985; and Kroner et al., *Process Biochem.*, 19:170–179 (1984). Kroner et al. concluded that aqueous two phase conversion was economically the best method for production of enzymes providing that the cost of chemicals for creation of the two phases could be contained by recycling or reduction in the amount required by modification of the phase systems.

Aqueous two phase systems formed from poly(ethylene glycol) (PEG) and a salt, usually potassium phosphate or ammonium sulfate, have long been used for purification of enzymes in the laboratory. This system is economically viable on an industrial scale due to the low cost of the chemicals required to make up the phase system. Tjerneld, "Aqueous two phase partitioning on an industrial scale", in *Poly(Ethylene Glycol) Chemistry: Biotechnical and Biomedical Applications,* J. Milton Harris, Ed., Plenum Press, New York, 1992. However, there are certain disadvantages with the PEG-salt system. The high concentrations of salt present can be tolerated by many proteins but not by a cell or organelle. Per-Ake-Albertsson, *Partition of Cell Particles and Macromolecules,* 3rd Edn., John Wiley & Sons, New York, 1986. To encompass such sensitive separations, a much milder system is required in which salt is replaced by another polymer. High concentrations of salt may also interfere with affinity partitioning in which a biospecific ligand is bound to the PEG-rich phase. Johansson, G., *Methods Enzym.,* 228:64–74 (1994); and Johansson, G., "Affinity Partitioning in PEG-containing Two phase Systems", in *Poly (Ethylene Glycol) Chemistry: Biotechnical and Biomedical applications,* J. Milton Harris, Ed., Plenum Press, New York, 1992. On an economic industrial scale, high concentration of phosphate and sulfate in effluent streams pose an economic and environmental problem. Kroner et al., Process Biochem., 19:170–179 (1984); and Tjerneld, "Aqueous two phase partitioning on an industrial scale", in *Poly(Ethylene Glycol) Chemistry: Biotechnical and Biomedical Applications,* J. Milton Harris, Ed., Plenum Press, New York, 1992.

Aqueous two phase systems using two polymers offer a number of advantages over PEG-salt systems in the laboratory situation. Mixtures of unlike polymers in aqueous solution will generally separate into two phases with water contents ranging from 85–99%. Such a system is very mild, and the polymers appear to stabilize particle structure and biological activity. Mattiasson, B., *Methods Enzym.,* 137:657–667 (1988). Additionally there is an extremely low interfacial tension which does not damage delicate particles. Reproducible partitioning of macromolecules, cells and cell particles can be obtained under mild conditions. Per-Ake-Albertsson, *Partition of Cell Particles and Macromolecules,* 3rd Edn., John Wiley & Sons, New York, 1986.

The most commonly used two-polymer phase systems are of the PEG/dextran ("PEG-dx") type, using a synthetic hydrocarbon ether polymer and a sugar polymer which are mutually incompatible. Although alternatives to PEG are available, it remains the most widely used synthetic polymer for laboratory and commercial applications. Bamberger et al., "Preparation of Phase Systems and Measurements of their Physicochemical Properties" in *Partitioning in Aqueous Two Phase Systems: Theory, Methods, Uses and Applications to Biotechnology,* Academic Press, New York, 1985.

Dextran is available in a range of molecular weight fractions, however economic considerations preclude the use of fractionated dextrans on a large scale. Tjerneld and Johannsson, *Bioseparation,* 1:255–263 (1990). Crude dextran has been used for large-scale processes including semi-continuous enzymic hydrolysis of a model cellulose substrate and the enzymic hydrolysis of starch. Kroner et al., *Biotechnol. Bioeng.,* 24:1015–1045 (1982); Tjerneld et al., *Biotechnol. Bioeng.,* 27:1036–1043 (1985); Tjerneld et al., *Biotechnol., Bioeng.,* 27:1044–1050 (1985); and Larsson et al., *Biotechnol. Bioeng.,* 33:758–766 (1989). In these systems, the enzymes are retained in the lower dextran-rich phase, while the product is removed in the upper PEG-rich phase, which may be filtered and recycled. The high molecular weight fractions in crude dextran adversely affect the partitioning of the enzyme to the bottom phase so that some is lost in the top phase. This may be partially offset by the use of higher molecular weight PEG and the fact that lower concentrations are required for separation. However, the systems are considerably more viscous than those using fractionated dextrans. Moreover, the use of crude dextran only results in a four-fold reduction in cost over the use of fractionated dextrans. Kroner et al., Process Biochem., 19:170–179 (1984). Hydroxypropyl starch (HPS) derivatives have been evaluated as possible replacements for fractionated dextrans. Ling et al., *Carbohydr. Polymers,* 11:43–54 (1989); and Sturesson et al., *Appl. Biochem. Biotech.,* 26:281–295 (1990).

Pullulan is a microbial polysaccharide which has been used in the form of a PEG-pullulan system for semi-continuous production of cellulases as well as batch separations of enzymes. Nguyen et al., *Appl. Microbiol. Biotechnol.*, 27:341–346 (1988). Pullulan, however, can cause viscosity difficulties at higher concentrations. Maltodextrins from corn starch (molecular weight average 1200, 1800, 3600) have been proposed as a low cost alternative to fractionated dextrans. Szlag et al., *ACS Symposium Series* 419:71–86 (1990); and Szlag and Giuliano, *Biotechnol. Techniques*, 2:277–282 (1988). Because of the lower molecular weight of the maltodextrins, higher concentrations are required to achieve phase separation. The maltodextrins also are susceptible to starch degrading enzymes, which could be a significant consideration in industrial scale bioconversion in which the sugar polymer would be exposed to the enzyme for long periods.

There is a need for the development of improved aqueous two phase systems for the partitioning of biological materials. It is therefore an object of the invention to provide methods for separating biological materials from cells and other debris using aqueous two phase systems. It is another object of the invention to provide aqueous two phase extraction systems containing enzymes for use in bioconversion applications. It is a further object of the invention to provide aqueous two phase systems which can be used to partition biological materials such as cells and macromolecules without degrading or modifying the materials, and without affecting biological activity of the materials.

SUMMARY OF THE INVENTION

Aqueous multiphase systems which permit the extractive separation of a biological material from a solution mixture are provided, wherein an aqueous solution of arabinogalactan defines at least one phase, and an aqueous solution of a second solute defines at least one other phase. In a preferred embodiment, an aqueous two phase system is provided in which one phase is defined by an aqueous solution in which arabinogalactan is the predominant solute, and the other phase is defined by an aqueous solution in which another polymer, such as a poly(ethylene glycol), is the predominant solute. Biological materials which can be extracted from a solution mixture using the aqueous multiphase systems include biological materials such as cells, organelles, macromolecules such as antibodies and enzymes, and small organic molecules. The aqueous two phase systems can be used in wide range of different applications to separate biological materials from cells and other debris in a mixture. For example, the systems can be provided with an enzyme and used in bioconversion applications to produce a product which is selectively soluble in one of the phases. The aqueous two phase systems can be used to extract biological materials from different mixtures inexpensively on a large scale.

DETAILED DESCRIPTION OF THE INVENTION

Figure 1:
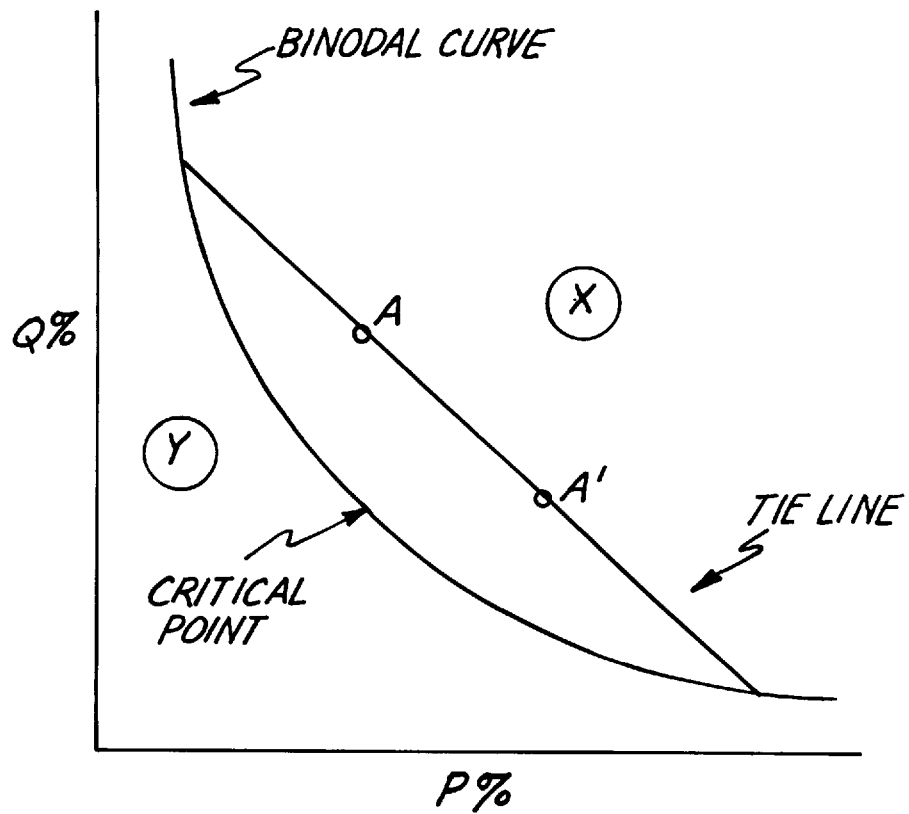
FIG. 1 is a phase diagram for an aqueous two phase system of components P and Q.

Methods are provided for the separation of biological materials using aqueous multiphase systems containing arabinogalactan. In one embodiment, improved aqueous two phase systems are provided, wherein at least one phase is defined by an aqueous solution of arabinogalactan, and the other phase is defined by an aqueous solution of a polymer such as poly(ethylene glycol). The aqueous two phase systems containing arabinogalactan can be used in a wide variety of biotechnology applications for the extractive separation of biological materials such as macromolecules, cells, cell structures, organelles and organic molecules, from microbial or other sources. The aqueous two phase systems also can be used for large scale recovery of fermentation products by extractive bioconversion and for the separation of enzymes. Arabinogalactan also can be used in two phase systems as a biologically specific polymer for certain specialized extractions. The extraction process can be used repeatedly, resulting in resolution to several fractions of ever greater purity, and the components of the multiphase system can be recycled after each extraction.

I. Formation of Aqueous Multiphase Systems

The aqueous multiphase systems include an aqueous solution of arabinogalactan defining one phase, and an aqueous solution of another solute, such as a poly(alkylene glycol), defining at least one additional phase. The formation and use of aqueous two phase systems to separate components in aqueous solution has been described, for example, in: Per-Ake-Albertsson, *Partition of Cell Particles and Macromolecules*, 3rd Edn., John Wiley & Sons, New York, 1986; Walter, H. and Johansson, G., Eds., *Methods in Enzymology*, Vol. 228 (1994); and Bamberger et al., "Preparation of Phase Systems and Measurements of their Physicochemical Properties" in Partitioning in Aqueous Two phase Systems: Theory, Methods, Uses and Applications to Biotechnology, Academic Press, New York, 1985. Solutions can be dispensed by weight if their viscosity precludes accurate dispensation by volume.

The improved aqueous two phase systems described herein permit a selected biological material to be separated from a mixture of components by selectively extracting the target material into one phase of the two phase system. The selection of the solute forming the second phase, the choice of concentration of solutes in each of the phases as well as the concentration of buffers or salts in the phases, and the temperature of the phases, all can be selected depending on the target material to be separated. The target material then can be separated from the phase for example by methods such as membrane filtration, precipitation by non-solvent or by salting out.

A. Arabinogalactan

In the aqueous multiphase systems, at least one phase is an aqueous solution of arabinogalactan. Arabinogalactan is a water-soluble polysaccharide which can be isolated from species of the genus Larex. Arabinogalactan may constitute up to 35% of the total heartwood of some species. Stout, "Larch Arabinogalactan" in *Industrial Gums*, R. L. Whistle Ed., Academic Press, New York, pp. 307–310, 1959. It is highly soluble and can be obtained at 95% purity from larch chips. Impurities present are largely monomeric sugars, polyphenols and salts. In a preferred embodiment, highly purified ultrarefined arabinogalactan is used. Methods for the preparation of ultrarefined arabinogalactan are disclosed in U.S. Pat. No. 5,116,969, the disclosure of which is incorporated herein by reference. Ultrarefined arabinogalactan of greater than 95%, or greater than 99.9% purity (Larex UF™) is available from Larex, International, St. Paul, Minn.

Arabinogalactan provides a useful low cost alternative to the use of fractionated dextrans in aqueous two phase extractions of biological material. Arabinogalactan from Larex species is useful since it is extremely water-soluble, occurs naturally with a very narrow molecular weight distribution, and is highly branched and thus not subject to viscosity problems. In addition, arabinogalactan can be used in the presence of enzyme systems which degrade other polysaccharides.

The structure and physical properties of arabinogalactan make it useful as one component of the aqueous multiphase systems for the extraction of biological materials. The structure of arabinogalactan has been partially elucidated. Timell, *Adv. Carbohydr. Chem.*, 20:409–483 (1965). It consists of a backbone of galactopyranose residues linked mainly β(1→3) although variations have been encountered in which some (1→6) linkages are found in the main chain. This chain is highly-branched bearing side-chains on 0–6 of many residues. The side-chains may contain one or more galactopyranose residues or arabinofuranose and less commonly arabinopyranose residues.

Calculations based upon viscosity indicate that the molecule has a spherical shape when dissolved in water. Increasing concentrations of arabinogalactan have been found to lower the interfacial tension between water and liquid petrolatum or mineral oil. Nazereth et al., *J. Pharm. Sci.*, 50:560–563 (1961); Nazareth et al., *J. Pharm. Sci.*, 50:564–567 (1961); H. S. Owens, *J. Am. Chem. Soc.*, 62:930–932 (1940); and Ekman and Douglas, *Tappi*, 45:477–481 (1962). The polydispersity of highly purified arabinogalactan is very low. Thus, the physical properties of arabinogalactan make it highly suitable for laboratory and industrial-scale two phase separations.

The concentration of arabinogalactan in the aqueous phase can be modified for a particular application depending on the target material to be separated. For example, a concentration of arabinogalactan ranging from about 2 to 40% weight/weight (w/w), can be used, and in a preferred embodiment, from about 6 to 30%. In a preferred embodiment, the molecular weight of the arabinogalactan is between about 10,000 and 30,000 daltons (by size exclusion chromatography with pullulan reference). The temperature of the two phase system containing arabinogalactan in one embodiment can range from about 20° to 90° C., and in a preferred embodiment, ranges from about 25° to 70° C.

B. Specific Binding of Arabinogalactan

Arabinogalactan exhibits binding specificity for certain biological substrates. Carbohydrate binding lectins are present in both plants and animals, and certain lectins will bind terminal galactose residues. Kobata, A., *Acc. Chem. Res.*, 26:319–324 (1993). The binding of cluster ligands to mammalian hepatocyte lectin has been examined. Lee et al., *Biochem.*, 23:4255–4261 (1984). These ligands have varying numbers and lengths of branches terminating in galactose residues. The presence of three terminal β-galactopyranose residues linked by flexible branches and chains yields very strong binding both to the hepatocyte and to the isolated lectin. Similar substructures are present in arabinogalactan and it is accordingly readily bound by hepatocytes. This property has been exploited for the delivery of drugs to the liver and to block experimental metastasis formation. Gronman et al., *Bioconjugate Chem.*, 5:547–556 (1994); and Hagmar, B., *Zentralbl. Bakteriol., Suppl.*, 25:138–145 (1994). Arabinogalactans have also been shown to interact with human cytotoxic monocytes. Muchmore et al., *Immunobiol.*, 158:191–206 (1981).

Lectins in plants are also associated with arabinogalactan. Yates, E. A., *Carbohydr. Polymers.*, 24:281–286 (1994); and Majumdar and Surolia, *Experientia*, 34:979–980 (1978). Arabinogalactan-proteins are secreted upon the stigma surface of flowers, and it has been suggested that they are involved in the capture and adhesion of pollen grains. Clarke et al., *Proc. Natl. Acad. Sci. U.S.A.*, 76:3358–3362 (1979).

The biological binding specificity of arabinogalactan permits it to be used in specialized extractions, for example the binding of cells in a lower phase as products of bioconversion are removed in the top phase. Thus, in addition to supplying a low-cost alternative to fractionated dextrans for aqueous two phase systems, the specific interactions of arabinogalactan permit the selective separation of certain components such as cells, proteins and organelles in aqueous two phase systems.

C. Other Solutes Used to Define the Aqueous Phases

The multiphase systems for the extractive separation of biological materials include, in addition to the aqueous phase containing arabinogalactan, one or more additional aqueous phases. The phases are designed to permit the selective extraction of a target material to one of the phases. In one type of embodiment, the second phase is an aqueous solution of a polymeric ether such as a poly(alkylene oxide). In a preferred embodiment, a poly(alkylene glycol) may be used. As used herein the term "poly(alkylene glycol)" includes poly(alkylene glycols) and derivatives thereof. For example, poly(ethylene glycols) or poly(propylene glycols) or copolymers or mixtures thereof can be used. The terms "poly(ethylene glycol)" or "poly(propylene glycol)" also include derivatives thereof made using chemical modifications and reagents available in the art.

Non-limiting examples of poly(ethylene glycols) ("PEGs") which may be used include, for example, E series poly(ethylene glycol), available from Dow Chemical Co., Midland, Mich., such as E8000 and E4500 ($M_w$ 8000 and 4500 daltons), as well as other molecular weights such as 900 or higher. These PEGs are solid white powders. "*The Polyglycol Handbook*", Dow Chemical Co., 1988. The molecular weight of the PEG thus may range from, for example, 1,000 to 8,000 daltons or greater. The concentration of PEG, for example of molecular weight 8,000 can range from, e.g., 1 to 20%, and in a preferred embodiment, 6 to 10% (w/w).

Optionally, biospecific affinity ligands, such as antibodies can be attached to one or more of the polymers, such as PEG, used to form the aqueous two phase system, using methods available in the art. The affinity of biospecific ligands attached to a polymer will strongly affect partitioning of substances in the multiphase systems. For example, dextran has been modified to increase the partitioning of an enzyme to the lower phase. Hayashida et al., *J. Ferment. Bioeng.*, 69:240–243 (1990).

II. Characterization of Multiphase Systems

A. Phase Diagrams

Phase diagrams of aqueous two phase systems can be obtained using methods available in the art. An exemplary phase diagram of an aqueous two phase system of P and Q is illustrated in FIG. 1. Per-Ake-Albertsson, *Partition of Cell Particles and Macromolecules*, 3rd Edn., John Wiley & Sons, New York, 1986; Bamberger et al., "Preparation of Phase Systems and Measurements of their Physicochemical Properties" in *Paritioning in Aqueous Two phase Systems: Theory, Methods, Uses and Applications to Biotechnology*, Academic Press, New York, 1985; and Brooks and Norris-Jones, *Methods Enzymol.*, 228:14–27 (1994). Factors which affect phase formation of a polymer solution include temperature, molecular weight of the polymers, viscosity, density and polydispersity of the polymers used.

Mixtures whose composition fall in the region above the binodal curve (X) will have two phases; below the binodal curve (Y) they will have one phase. At the critical point, the volumes and the compositions of the phases become equal; mixtures whose composition is close to the critical point are difficult to work with, since slight variations will radically affect separation and two phases may readily become one. The tie line connects mixtures (e.g., A,A') which have the same phase composition but different total compositions and phase volumes.

Binodal curves of arabinogalactan containing two phase systems can be obtained by turbidometric titration. Albertsson and Tjerneld, "Phase Diagrams", in *Meth. Enzymol.,* 228:3–13 (1994). Spectrophotometric measurements of turbidity also can be used. Larsson and Mattiasson, *Biotechnol. Bioeng.,* 31:979–983 (1988). Tie lines can be determined by sampling of phases and analysis by polarimetry or refractive index. Per-Ake-Albertsson, *Partition of Cell Particles and Macromolecules,* 3rd Edn., John Wiley & Sons, New York, 1986; Bamberger, et al., "Preparation of Phase Systems and Measurements of their Physicochemical Properties" in *Partitioning in Aqueous Two phase Systems: Theory, Methods; Uses and Applications to Biotechnology,* Academic Press, New York, 1985; and Brooks and Norris-Jones, *Meth. Enzymol.,* 228:14–27 (1994). Critical points can be determined by construction of a perpendicular to the mid-points of tie lines close to the critical point. Per-Ake-Albertsson, *Partition of Cell Particles and Macromolecules,* 3rd Edn., John Wiley & Sons, New York, 1986. Viscosities can be determined where appropriate by capillary viscometry.

The binodal curve changes with temperature, this change having most effect upon phase systems near the critical point. At some temperature, phase separation may not occur. The range of temperatures over which two polymers will separate is important since it will affect the range of possible extractions which may be effected. Polymer combinations can be selected which permit phase separation at a preselected temperature. A polymer combination can be selected which permits bioconversion to be conducted at higher temperature which maximizes conversion. For example, activity of cyclodextrin glycosyl transferase (CGTase) [EC 2.4.1.19] from Thermoanaerobacter sp. ATCC 53627, which is used in the industrial production of cyclodextrins, has maximum activity at 95–100° C. Starnes, R. L., *Cereal Foods World,* 35:1094–1099 (1990).

In general, the higher the molecular weight of the polymers, the lower is the concentration required for phase separation. Separation may be regarded as occurring because of interactions between molecules. In aqueous two phase systems formed using arabinogalactan and PEG, the hydrophilic arabinogalactan and the relatively hydrophobic PEG mutually repel each other. These repulsive interactions increase with increasing molecular size, as they are the sum of the interactions of all the individual segments of the molecules.

Viscosity of individual phases increases with increasing molecular weight. Increasing viscosity increases separation times and this effect is strongest when the largest phase is the most viscous. Separation may be accelerated by centrifuging. Usually the polymer which enriches the densest phase does so at all compositions, but this is not true for all systems. Increasing polydispersity (range of molecular weights) of the polymers causes the loss of a sharp transition to two phases. Instead regions where the mixtures are more or less turbid are encountered. This results in a nonuniform broadening of the binodal curve. A method for characterizing phase systems containing polydisperse components has been described. Larsson and Mattiasson, *Biotechnol. Bioeng.,* 31:979–983 (1988). In a preferred embodiment, the polydispersity of the arabinogalactan and the other polymer used to form the two phase system is minimal.

B. Partitioning Coefficients: Factors Effecting Partitioning

Materials will partition within the two phase systems depending on the various properties of the materials and the polymers which are used to form the phases. Thus, the systems can be designed to promote partitioning of the target material in a selected phase. The partition coefficient, K, of a soluble substance in an aqueous two phase system is defined as:

$$K = \frac{\text{upper phase concentration}}{\text{lower phase concentration}}$$

Particles such as cells and organelles can concentrate at the interface to a greater or lesser extent depending upon the composition of the phase system. Walter and Larsson, *Methods Enzymol.,* 228:42–63 (1994); and Hosono and Hahn-Hagerdal, *Biochim. Biophys. Acta,* 855:182–192 (1986). The physics of partition of particles is complex. Per-Ake-Albertsson, *Partition of Cell Particles and Macromolecules,* 3rd Edn., John Wiley & Sons, New York, 1986. Certain parameters can have an effect upon the partition coefficient, such as interfacial tension, molecular weight of polymers, surface area of particles, dissolved salts, biospecific affinity and temperature. At the critical point where interfacial tension is extremely low, cells will partition to one or other of the phases. Increasing interfacial tension associated with increase in the concentration of the polymers will favor the interface or even remove the particles into the opposing phase. In the absence of an electrical potential, weaker hydrophobic interactions also will affect partitioning.

Increasing the molecular weight of one polymer will favor the phase rich in the polymer of lowest molecular weight. This effect is not uniform but is greatest for high molecular weight substrates. Increasing surface area decreases the partition coefficient in an exponential manner. The effect of dissolved salts depends upon the types and ratios of different ions but is almost independent of concentration. Salts partition unequally resulting in a potential difference between phases thus affecting the distribution of charged species such as proteins.

III. Materials Which Can Be Separated

The aqueous two phase systems can used to separate a wide range of materials. Biologically active materials can be separated without loss of biological activity. Biological materials which can be separated from cells, cell debris and other components of a solution include cells, cell structures such as organelles, macromolecules and organic molecules. The aqueous two phase system can be adapted for a particular material being separated. For example, the polymer or polymer concentration can be varied, or different buffer systems can be used, as described herein.

Biological macromolecules which can be separated by extraction in the aqueous two phase systems include lipids, nucleic acids, carbohydrates, amino acids, organic molecules, and proteins such as enzymes and antibodies. Proteins in the phases can be assayed using a bovine serum albumin (Sigma Chemical Co., St. Louis, MO) standard. Stoscheck, C. M., *Methods in Enzymology,* 182:50–68 (1990); Lowry et al., *J. Biol. Chem.,* 193:265–275 (1951); Layne, E., *Methods in Enzymology,* Volume 3 (1957). Proteins which can be separated include enzymes, and antibodies such as immunoglobulin G. Proteins advantageously can be separated without precipitation problems which occur using PEG-dextran systems.

Enzymes which can be partitioned in the arabinogalactan-containing two phase systems include proteases and lipases. Additionally, enzymes used in the industrial hydrolysis of starch, such as glucoamylase [EC 3.2.1.3] and α-amylase

[EC 3.2.1.1] can be isolated. Larsson et al., *Biotechnol. Bioeng.*, 33:758–766 (1989). Partitioning may be assessed by assay as protein or by comparing relative rates of activity against substrate. Hayashida et al., *J. Ferment. Bioeng.*, 69:240–243 (1990).

Other enzymes which can be partitioned include cyclodextrin glycosyl transferase—CGTase [EC 2.4.1.19] which can be obtained extracellularly by cultivation of Thermoanaerobacter sp. ATCC 53627. Starnes, R. L., *Cereal Foods World*, 35:1094–1099 (1990). Additionally, particles, such as pollen, or cells such as hepatocytes, and cell fragments can be separated using the arabinogalactan-containing aqueous two phase systems.

IV. Bioconversions

Bioconversions also can be conducted in the aqueous two phase systems. In this embodiment, to isolate the product of an enzyme reaction, the two phase system is provided with an enzyme substrate and an enzyme which are confined to one of the phases, wherein the enzyme is capable of reacting with the substrate to produce a product that is more soluble in the other phase. In the bioconversion, the enzyme in the system converts the substrate into product, and the product is selectively concentrated into the other phase, to permit the separation of the product from other materials in the system such as enzyme or enzyme substrate, and to minimize substrate inhibition of the enzyme.

Small molecules which are substrates and products of bioconversion can be partitioned in the aqueous two phase systems, such as ethanol, cyclodextrins, acetone, butanol and glucose. Two phase systems including arabinogalactan can be used which overcome unfavorable partitioning which has been reported to be a problem in other systems. Mattiasson, B., *Methods Enzym.*, 137:657–667 (1988). Concentrations of components of the bioconversion in the two phase solution can be assayed by liquid chromatography using a reverse phase column eluted with water (8% aqueous MeOH for cyclodextrin) and refractive index detection, or by colorimetric analysis.

Arabinogalactan containing two phase systems can be used in bioconversions in, for example, the enzymic hydrolysis of cellulose or starch. Tjerneld et al., *Biotechnol. Bioeng.* 27:1036–1050 (1985); and Larsson et al., *Biotechnol. Bioeng.*, 33:758–766 (1989). This type of use for two phase systems has recently been reviewed. Harris, J. M., Ed., *Poly(ethylene glycol) Chemistry, Biotechnical and Biomedical Applications,* Plenum Press, N.Y., Chapter 6, pp. 85–101, 1992.

Aqueous two phase systems can be used, for example, in bioconversion processes to produce cyclodextrins. The enzyme cyclodextrin glycosyl transferase [EC 2.4.1.19] is used for the industrial production of cyclodextrins. A variety of methods have been investigated for large scale industrial bioconversion to form cyclodextrins, including immobilization of the enzyme on resins or inorganic supports, the use of membrane bioreactors coupled with ultrafiltration and reverse osmosis and an agitated bead reaction system. Rozell, J. D., U.S. Pat. No. 4,921,796; Kim et al., *Biotechnol. Bioeng.*, 41:88–94 (1993); Hashimoto et al., *Denpun Kagaku,* 32:307–311 (1990); and Han and Lee, *Sanop Misaengmul Hakhoechi,* 19:163–170 (1991). A variety of small molecules have demonstrated an ability to enhance the bioconversion. Lee and Kim, *Enzym. Microb. Technol.*, 13:499–503 (1991). Low molecular weight poly(ethylene glycol) and poly(propylene glycol) have been shown to enhance production of cyclodextrins by changing the conformation of the substrate and inhibiting hydrolytic activity by the enzyme. Delbourg et al., *Biotechnol. Lett.*, 15:157–162 (1993); and Hayashida and Kawakami, *J. Ferment. Bioeng.*, 73:239–240 (1992).

The aqueous two phase systems containing arabinogalactan described herein offer a low cost and efficient alternative method for producing cyclodextrins in bioconversions. In the separation, the equilibrium can be drastically shifted in favor of cyclodextrin production by removal of the cyclodextrin by addition of molecules that specifically complex the cyclodextrins, such as cyclohexane or C12 cyclic compounds. F. C. Armbruster, "The Use of Cyclohexane in the Production of Pure α- and β-Cyclodextrins", *Proc. Fourth Int. Symp. Cyclodextrins,* O. Huber and J. Szejtl, Eds., pp. 33–39 (1988); and Rendleman, J. A., *Carbohydr. Res.*, 230:343–359 (1992). Aqueous two phase systems may be designed with the appropriate buffers, polymers, temperature and other appropriate conditions for the enzyme/substrate system used in the bioconversion process.

The invention will be further understood from the following non-limiting examples.

EXAMPLE 1

Phase Diagram of an Arabinogalactan-PEG solution

A two phase system was formed which included one phase consisting of arabinogalactan (AG) in aqueous solution and a second phase of PEG 8000 in aqueous solution. High-purity arabinogalactan from Western Larch, Larex UF™, $[\alpha]_D^{28}$+11.1° (c=4.04, H$_2$O) was used, which is available from Larex International, St. Paul, Minn. This arabinogalactan, using size-exclusion chromatography (SEC) (Shodex KB-804), has a narrow distribution of $M_W$ in the 17,000 range (referenced to pullulan standards), and has been shown to have a polydispersity of <1.5. Kobata, A., *Acc. Chem. Res.*, 26:319–324 (1993).

Figure 2:
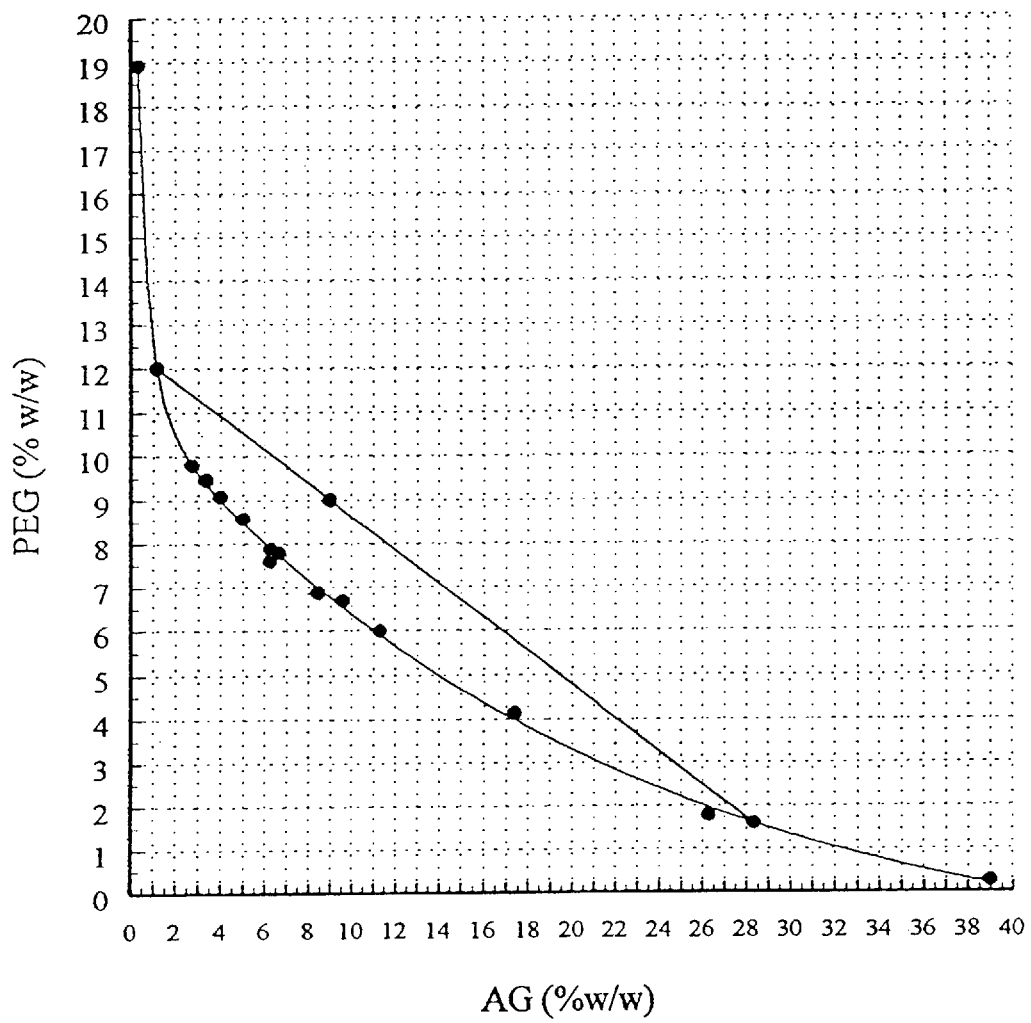
FIG. 2 is a phase diagram for an aqueous two phase system of arabinogalactan and poly(ethylene glycol).

Using the Larex UF™ and PEG 8000, a binodal curve was constructed by turbidometric titration, which is shown FIG. 2. In the phase diagram, the region above the line represents the two phase mixtures and the region below the line represents homogeneous solutions. This diagram indicates this system can be used as an aqueous two phase system.

In another example, the composition of an aqueous two phase system containing 20% Larex UF™ and 20% PEG-4500 was examined qualitatively by SEC (Shodex KB-804) using refractive index detection. Larex UF™ was confined primarily to the lower phase and PEG to the upper with only a trace of PEG in the lower phase.

EXAMPLE 2

Separation of β-Cyclodextrin

β-cyclodextrin was dissolved in a 20% aqueous solution of Larex UF™ and an equal volume of 20% aqueous PEG-8000 added. After shaking, the mixture was centrifuged and the two phases examined by liquid chromatography (C-18/8% aqueous MeOH) by refractive index detection. This indicated that the β-cyclodextrin had a partition coefficent (upper/lower) of 2.0. The hydrophobic interior of the cyclodextrin molecule possibly complexes with the PEG molecule in the separation.

EXAMPLE 3

Distribution Coefficients of Substances in Arabinogalactan/PEG Phase Systems

Two-phase systems of total weight 10.0 g in 0.1M, pH 4.5 sodium acetate buffer, containing 16% (w/w) arabinogalactan and 6% PEG 8000, were prepared and mixed with the following substances before equilibration at 25° C. for 30 minutes. Samples from upper and lower phases were analyzed for the added substance as indicated below.

(a) Bovine serum albumin, 0.27 g, analyzed by biuret.

(b) Amyloglucosidase (Sigma Chemical Co., type VI-B: from porcine pancreas), 16 mg, analyzed by soluble starch digest, using dinitrosalicylate (DNS) reagent and glucose reference.

(c) Corn starch, 1.0 g, analyzed by blue value.

(d) Glucose, 0.6 g, analyzed by DNS.

(e) α-amylase (Sigma Chemical Co., type VI-B: from porcine pancreas), 16 mg, analyzed as in (b).

The distribution coefficients, K (concentration in upper layer/concentration in lower layer) in AG (16%): PEG 8000 (6%) in 0.1M, pH 4.5, sodium acetate buffer at 25° C. are provided below in Table 1.

TABLE 1

Distribution Coefficients in an Arabinogalactan: Poly(Ethylene Glycol) Two Phase System

|  | K (upper/lower) |
|---|---|
| Bovine serum albumin | 0.057 |
| Amyloglucosidase | 0.15 |
| Corn starch | 0.0 |
| Glucose | 1.17 |
| α-Amylase | 0.26 |

EXAMPLE 4

Conversion of Starch to Glucose

The two-phase system of Example 3 was prepared with the addition of 16 mg amyloglucosidase and 1.0 g cornstarch. The mixture was stirred at 55° C. for 90 min, then allowed to settle at 25° C. for 15 min. All of the remaining solid starch was in the lower layer and analysis of the upper layer showed 41.9 mg and apparent glucose per g of phase. Using the distribution coefficient for glucose from Table 1, this corresponds to 48% conversion of starch.

When the same experiment was repeated in the absence of arabinogalactan and PEG (i.e., a homogeneous buffer system) the corresponding conversion of starch was 26%. The increased starch conversion results from reduced product inhibition of the enzyme in the two-phase system.

EXAMPLE 5

Partitioning of PEG Derivatized with an Affinity Ligand

Equal volumes of a 30% solution of PEG-6000 and 20% Larex UF® gave complete separation in less than 20 minutes, without centrifuging, to yield a bottom phase:top phase ratio of 1:2. PEG-3000 with the affinity ligand Cibacron blue 3GA covalently attached was completely confined to the upper, PEG-rich phase.

Modifications and variations of the present invention will be obvious to those skilled in the art from the foregoing detailed description. Such modifications and variations are intended to come within the scope of the following claims.

What is claimed is:

1. A method for separating a target material from a mixture, the method comprising:
   i) providing an aqueous multiphase system comprising:
      an aqueous solution comprising arabinogalactan defining a first phase; and
      an aqueous solution comprising a solute defining at least a second phase; and
   ii) extracting a mixture comprising a target material with the multiphase system, thereby to selectively concentrate the target material in one of the phases and to separate the target material from the mixture.

2. The method of claim 1 wherein the system is a two phase system and wherein the material is a biological material.

3. The method of claim 2 wherein the material is biologically active, and wherein the biological activity of the material is preserved after the extraction step (ii).

4. The method of claim 2 wherein the biological material is selected from the group consisting of amino acids, carbohydrates, organic molecules, proteins, nucleic acids, and lipids.

5. The method of claim 2 wherein the biological material is selected from the group consisting of pollen, cells and cell fragments.

6. The method of claim 2 wherein the biological material is selected from the group consisting of yeast and hepatocytes.

7. The method of claim 2 wherein the arabinogalactan is ultrarefined.

8. The method of claim 2 wherein the concentration of the arabinogalactan in the first phase is between 2 and 40% (w/w).

9. The method of claim 2 wherein the solute in the second phase is a poly(alkylene glycol).

10. The method of claim 9 wherein the poly(alkylene glycol) is selected from the group consisting of a poly (ethylene glycol), a poly(propylene glycol) and copolymers and mixtures thereof.

11. The method of claim 9 wherein the poly(alkylene glycol) is a poly(ethylene glycol) attached to an affinity ligand.

12. The method of claim 2 wherein the arabinogalactan is capable of selectively binding the target material, and wherein, in step (ii), arabinogalactan specifically binds the target material, thereby concentrating the target material in the first phase.

13. The method of claim 2 for conducting a bioconversion, wherein the target material is the product of an enzyme reaction; and
   wherein step i) further comprises providing in the system an enzyme substrate and an enzyme capable of reacting with the substrate to produce a product that is preferentially soluble in one of the phases; and
   wherein step ii) further comprises permitting the enzyme in the system to convert the substrate to the product, and selectively concentrating the product into the other phase, thereby to isolate the product.

14. The method of claim 13 wherein the enzyme is selected from the group consisting of protease, glycanase and lipase enzymes.

15. The method of claim 1 wherein the arabinogalactan is isolated from a tree of the genus Larix.

16. The method of claim 1 wherein the solute is a polymer.

17. An aqueous multiphase system for separating a target material from a solution mixture, the multiphase system comprising:
   an aqueous solution of arabinogalactan defining a first phase; and
   an aqueous solution of a solute defining at least a second phase;
   wherein the multiphase system is capable of separating a target material from a mixture selectively into one of the phases, upon extraction of the mixture with the multiphase system.

18. The multiphase system of claim 17 wherein the system is a two phase system and wherein the material is a biological material.

19. The aqueous two phase system of claim 18 wherein the biological material is selected from the group consisting of amino acids, carbohydrates, organic molecules, proteins, nucleic acids, lipids, cells and cell fragments.

20. The aqueous two phase system of claim 18 wherein the arabinogalactan is ultrarefined.

21. The aqueous two phase system of claim 20 wherein the concentration of arabinogalactan in the first phase is between about 2 and 40% (w/w).

22. The aqueous two phase system of claim 18 wherein the solute in the second phase is a poly(alkylene glycol).

23. The aqueous two phase system of claim 22 wherein the poly(alkylene glycol) is selected from the group consisting of a poly(ethylene glycol), a poly(propylene glycol) and copolymers and mixtures thereof.

24. The aqueous two phase system of claim 22 wherein the poly(alkylene glycol) is a poly(ethylene glycol) attached to an affinity ligand.

25. The aqueous two phase system of claim 18 for conducting a bioconversion to produce an enzyme product, wherein the system further comprises an enzyme capable of reacting with a substrate in one phase to produce a product which is more soluble in the other phase.

26. The aqueous two phase system of claim 25 wherein the enzyme is selected from the group consisting of protease, glycanase and lipase enzymes.

27. The aqueous two phase system of claim 18 wherein the arabinogalactan is isolated from a tree of the genus Larix.

28. The aqueous two phase system of claim 18 wherein the solute is a polymer.

* * * * *

UNITED STATES PATENT AND TRADEMARK OFFICE
CERTIFICATE OF CORRECTION

PATENT NO. : 5,882,520
DATED : March 16, 1999
INVENTOR(S) : Richards et al.

It is certified that error appears in the above-identified patent and that said Letters Patent is hereby corrected as shown below:

Title page,
Item "[56] References Cited U.S. Patent Documents", insert -- 5,772,876 6/1998 Murakami --; and
Item "[21] Appl. No.:", delete "548,849", and insert -- 08/548,849 --.

Signed and Sealed this

Twenty-eighth Day of August, 2001

Attest:

NICHOLAS P. GODICI
Attesting Officer
Acting Director of the United States Patent and Trademark Office